(12) United States Patent
Tani et al.

(10) Patent No.: US 7,170,970 B2
(45) Date of Patent: Jan. 30, 2007

(54) FLUORESCENT X-RAY ANALYSIS METHOD AND FLUORESCENT X-RAY ANALYSIS APPARATUS

(75) Inventors: Yoshiyuki Tani, Neyagawa (JP); Hiroshi Iwamoto, Toyonaka (JP); Takao Hisazumi, Ibaraki (JP); Yukihiro Iwata, Ibaraki (JP); Etsuyoshi Sakaguchi, Ibaraki (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 11/197,303

(22) Filed: Aug. 5, 2005

(65) Prior Publication Data

US 2006/0029182 A1   Feb. 9, 2006

(30) Foreign Application Priority Data

Aug. 6, 2004   (JP) ............... P2004-230441

(51) Int. Cl.
   *G01N 23/223*   (2006.01)
(52) U.S. Cl. .................... 378/45; 209/589
(58) Field of Classification Search ............ 378/44–49; 209/589
   See application file for complete search history.

(56) References Cited

U.S. PATENT DOCUMENTS

| | | | |
|---|---|---|---|
| 3,562,525 A * | 2/1971 | Constantine et al. | 378/48 |
| 3,980,568 A * | 9/1976 | Pitchford et al. | 378/46 |
| 5,570,408 A | 10/1996 | Komatani | |
| 6,324,251 B1 | 11/2001 | Kuwabara | |
| 6,519,315 B2 * | 2/2003 | Sommer et al. | 378/45 |
| 6,647,283 B2 * | 11/2003 | Klotz | 600/425 |

FOREIGN PATENT DOCUMENTS

| | | |
|---|---|---|
| JP | 7-49319 A | 2/1995 |
| JP | 7-63711 A | 3/1995 |
| JP | 8-43329 A | 2/1996 |
| JP | 2000-121584 A | 4/2000 |
| JP | 2000-193615 A | 7/2000 |
| JP | 2000-199749 A | 7/2000 |
| JP | 2002-340822 A | 11/2002 |

OTHER PUBLICATIONS

WO 03/087215 A1, Composition of Materials Containing Recycled Plastics, Brian Riise et al., World Intellectual Property Organization, International Publication Date Oct. 23, 2003.*

* cited by examiner

*Primary Examiner*—Edward J. Glick
*Assistant Examiner*—John M. Corbett
(74) *Attorney, Agent, or Firm*—McDermott Will & Emery LLP

(57) ABSTRACT

The concentration(s) of element(s) contained in an unknown sample is measured without necessity of judging the sample relying on a human's eye and obtaining information from a supplier of the sample previously. The concentration(s) of trace element(s) such as Cd, Pb and Hg contained in parts for electronic or electric equipment is determined by (1) irradiating the sample with an X-ray so as to identify whether the type of the sample is a nonmetal-based material or a metal-based material; (2) selecting measuring conditions for a fluorescent X-ray analysis depending on the identified type of the sample; and (3) measuring the concentration(s) of one or more element(s) contained in the sample by the fluorescent X-ray analysis according to the selected measuring conditions.

9 Claims, 3 Drawing Sheets

FLUORESCENT X-RAY ANALYSIS METHOD AND FLUORESCENT X-RAY ANALYSIS APPARATUS

BACKGROUND OF THE INVENTION

The present invention is related to a fluorescent X-ray analysis method and a fluorescent X-ray analysis apparatus, particularly to the fluorescent X-ray analysis method which is suitable for detecting, at a high speed, environmental hazardous substances which may be mixed into mechanical parts for electric equipment and electronic equipment which parts have various compositions.

Recently, risk of the environmental hazardous substances which may be contained in parts which constitute electronic or electric equipment has been pointed out, and the contents of the environmental hazardous substances are restricted by laws or regulations in some countries and states. Directive of RoHs (Restriction of the use of certain Hazardous Substances in electrical and electronic equipment) will become effective as of July, 2006. This RoHs Directive inhibits the use of mechanical parts which contains cadmium (Cd), lead (Pb), mercury (Hg), certain brominated flame retardants (Polybrominated Biphenyls (PBB) and Polybrominated diphenyl ether (PBDE)) or hexavalent chromium (Cr(VI)) in an amount above threshold value. The threshold values for Cd, Pb, Hg, PBB, PBDE and Hg are respectively 1000 ppm, while the threshold value for Cr(VI) is 100 ppm. For this reason, it is necessary for electric and electronic equipment manufacturing companies to confirm that each part does not contain the environmental hazardous substance(s) above the threshold value.

As one method for measuring the content of a trace element, a fluorescent X-ray analysis method has been generally employed, which has a sensitivity of several tens ppm and allows nondestructive measurement. The procedure for quantifying the content(s) of element(s) contained in a sample by the fluorescent X-ray analysis is generally well known. For example, Japanese Kokai (Laid-Open) Patent Publication No. 8-43329/1996(A) discloses an example of the procedure.

A conventional procedure of the fluorescent X-ray analysis method is described below with reference to FIG. 3. As shown in FIG. 3, voltage and electric current conditions for an X-ray tube, a quantitative analysis method, and a measuring time (t) are set in the step 301. Next, the measuring is started (see the step 302). Subsequently, the measurement is carried out over the time "t" (see the step 303) and the measurement is finished (see the step 304). After finishing the measurement, the concentration(s) of the element(s) contained in a sample is calculated and the accuracy (standard deviation) of this calculation result is calculated so that the results as to the concentration(s) and the accuracy are obtained. Those results are displayed with displaying means such as an LCD and printed out by a printer (see the step 306).

Two major methods can be used as a quantification method for calculating the concentrations (that is, contents) of the elements contained in the sample. One is a "calibration curve method" wherein a calibration curve has been obtained by previously measuring the content of a target element and a shape of a spectrum, and the shape of the spectrum for the sample is compared with the calibration curve so as to determine the content of the element. The other is a "fundamental parameter (FP) method" wherein all the contained elements are identified and the content of each element is calculated from the spectrum (that is, the all the elements in the sample are quantified (the total of the elements is 100%)) on the assumption that the all the contained elements are reflected on the spectrum.

In general, the contents of trace elements contained in the sample made of, for example, a plastic which contains light elements such as C, H and O in large amounts are quantified by the calibration curve method, since the fluorescent light emission from the light elements is small. On the other hand, the quantification of the trace elements contained in the sample made of middle elements or heavy elements such as iron, zinc and tin is generally carried out by the FP method.

The conventional analysis methods, however, have the following problems:

(1) The exact results as to the concentrations may not be obtained unless the measuring parameters are exactly input, as carried out in the step 301; and (2) The measuring time tends to be set unnecessarily longer in order to determine the concentration(s) of the elements in the sample more accurately.

The problem (1) is particularly desired to be solved in the situation where a wide variety of parts should be analyzed quickly so as to comply with the RoHs directive. The determination of the measuring time and the selection of the quantification method (the calibration curve method or the FP method) are generally made according to the judgment by an operator. The judgment includes observing the sample to determine whether it is made of a metal or a plastic, based on his/her experience or information which has been given to him/her previously. The skill is required for determining the type or the kind of an unknown sample based on his/her experience, which makes the measurement inefficient. Particularly, the elements have to be quantified by the calibration curve method when the sample is made of a light metal such as aluminum or magnesium. The appearance of such a sample, however, may not be different from that of a sample made of a heavy metal such as iron. For this reason, even the skilled operator may often misjudge. Such misjudgment gives an erroneous result and causes confusion, and requires re-measuring, which reduces the measuring efficiency. The operator may avoid such misjudgment by obtaining the information as to the sample previously. However, the analysis conducted after obtaining the information cannot be said as an "unknown sample analysis" in a precise sense. This means that an effort is required to gathering the information, which reduces the measuring efficiency.

Next, the problem (2) is described by an example. Conventionally, when the content of Cd (which may be referred to as a "Cd concentration") in a plastic resin is measured by a fluorescent X-ray analysis method, the measuring time "t" is determined at the beginning of the measurement (as in step 301 in FIG. 3). In order to improve the accuracy of the measurement, the measuring time "t" is required to be very long, such as 200 seconds in the light of possibility of the presence of elements other than Cd. However, the volt and electric current in the X-ray tube may be set higher since the sample is a plastic-based one. Therefore, the 200-second measurement per sample may reduce the measurement efficiency in the situation where a large number of parts are required to be analyzed under the RoHs directive. The experiments conducted by the inventors showed that in the case where the Cd concentration such as 20 ppm is measured, 10 seconds is sufficient as the measuring time "t." In other words, whether the measuring time "t" is 10 seconds or 200 seconds, the results are the same from the viewpoint that the correct judgment is made as to whether or not the Cd concentration of the plastic sample is below the threshold value stipulated in the RoHs directive. On the other hand, it is necessary to restrict the volt and electric current in the X-ray tube upon measuring the Cd concentration in the sample whose main component is iron since the iron emits a fluorescent X-ray in a large amount. For this reason, a sufficiently long measuring time is required to obtain the counts of fluorescent X-ray from Cd in the sample with a sufficient accuracy. The experiment by the inventors showed that the measuring time should be about 100 seconds when measuring the Cd concentration of about 20 ppm for the sample whose main component is iron.

SUMMARY OF THE INVENTION

The present invention is made in the light of the above problems and the new knowledge obtained by the experiments. The object of the present invention is to provide a fluorescent X-ray analysis method which makes it possible to reduce the measuring time required for the quantification of the trace elements in an unknown sample, and to optimize the measuring conditions automatically depending on the sample, whereby the operability is improved.

The present invention provides a fluorescent X-ray analysis method which includes:

(1) identifying whether a sample type is a nonmetal-based material or a metal-based material by applying an X-ray to a sample;

(2) selecting measuring conditions for the fluorescent X-ray analysis depending on the sample type; and (3) measuring a concentration(s) of one or more elements contained in the sample by the fluorescent X-ray analysis according to the selected measuring conditions. The analysis method of the present invention is characterized in that the sample type (that is, whether the materials of the sample is nonmetal-based one or the metal-based one) is roughly judged from a fluorescent X-ray spectrum which is emitted from the sample resulting from application of an X-ray to the sample and the fluorescent X-ray analysis is carried out based on this judgment. Therefore, this fluorescent X-ray analysis method makes it possible to measure the contents of the trace elements (particularly, Cd, Pb, Hg, Br and Cr) contained in the unknown sample without necessity of the operator's task for determining the quantification method and the measuring time.

Herein, the term "nonmetal-based material" is used to refer to a material whose main component emits no or slight X-ray. The nonmetal-based materials include a plastic-based material, and a material whose main component is a light element whose atomic number is equal to or less than fifteen, such as aluminum or magnesium. It should be noted that although aluminum and magnesium are metal elements, these are referred to as nonmetal-based material for convenience herein. Further, it also should be noted that a material containing chlorine or bromine (the atomic numbers of these elements are at least fifteen, and therefore, these elements are not light elements in a precise meaning) is included in the nonmetal-based material for convenience as long as the material does not contain other middle elements or heavy elements, although the chlorine and bromine emit a fluorescent X-ray with a relatively high intensity.

The term "metal-based material" is used to refer to a material whose component is middle element or heavy element (specifically, the elements whose atomic number is at least sixteen) which emits a fluorescent X-ray in a large amount as a result of the application of X-ray. Specifically, the metal-based material includes the material whose main component is iron, zinc, copper, or tin.

In the above step (1), the sample type may be identified or judged by applying an X-ray to the sample for a short time, for example, 1 to 10 seconds. The metal-based materials emit the fluorescent X-ray with a high spectrum intensity by the short-time irradiation of X-ray, while the nonmetal-based materials except for the materials containing Cl or Br, emit no or slight fluorescent X-ray. Therefore, whether the sample is nonmetal-based material or metal-based material can be determined quickly by analyzing the energy and intensity of the spectrum The measuring conditions selected in the above step (2) is not limited to two types, one for the nonmetal-based material and the other for metal-based material. It should be noted that, in the step (2), the measuring conditions can be selected from various conditions considering that the types and concentration of the elements detected in the step (1), in addition to the sample type which is the nonmetal-based material or the metal-based material. The measuring conditions may be preferably selected from a predetermined list.

As described above, some nonmetal-based materials may contain Cl and/or Br. For these nonmetal-based materials, it is preferable that the measuring time is longer and the trace elements are quantified using a calibration curve which is different from the calibration curve used for quantifying the trace elements in the nonmetal-based material which does not contain Cl and/or Br. Therefore, the operation in the step (1) includes judging whether or not the sample contains Cl and/or Br, in addition to identifying whether the sample is the nonmetal-based material or the metal-based material. Specifically, when the intensity of the fluorescent X-ray due to Cl is higher than that due to the other elements in the fluorescent X-ray spectrum for a sample, and thereby the content of Cl is judged to be an order of percentage, the sample can be judged to contain Cl. It should be noted that the calibration curve used for the material containing Cl is not limited to one type, and several calibration curves for different contents may be prepared so that an appropriate one can be selected from these curves. Further, a hypothetical and intermediate calibration curve may be used, which may be made based on the calibration curves for the material containing Cl and for the material containing no Cl. These are applicable to Br.

In operation (1), the sample may be identified by a technique wherein the sample is identified as a metal-based material when at least one element selected from Fe, Zn, Cu and Sn is detected. The sample containing Fe, Zn, Cu or Sn gives a fluorescent X-ray spectrum wherein the spectral intensity of the fluorescent X-ray due to Fe, Zn, Cu or Sn is high, since these elements emit the fluorescent X-ray in a large amount. Specifically, when the intensity of the fluorescent X-ray due to any one of these four elements is significantly higher than those due to the other elements in the fluorescent X-ray spectrum for a sample, it can be said that the metal element is detected from the sample.

The present invention also provides a fluorescent X-ray analysis apparatus for carrying out the method of the present invention. The fluorescent X-ray analysis apparatus of the present invention includes a sample stage, an X-ray tube, a detector, and operation (or calculation) instrument, wherein the operation instrument includes:

means for identifying whether the sample type is a nonmetal-based material or a metal-based material, based on a fluorescent X-ray which is emitted from the sample by applying an X-ray to the sample;

means for selecting measuring conditions for a fluorescent X-ray analysis, depending on the identified sample type; and means for controlling each member in the analysis apparatus so that a concentration(s) of one or more elements contained in the sample is measured by the fluorescent X-ray analysis according to the selected measuring conditions. In other words, the operation instrument may be provided as an operation instrument configured to perform the following steps:

(1) classifying the sample as a nonmetal-based material or a metal-based material based on the communication received from the detector;
(2) selecting a measuring process condition from a predetermined list of measuring process conditions based on the classification of the sample; and
(3) controlling the X-ray tube so that concentration of at least one element contained in the sample may be measured according to the selected measuring condition; and
(4) determining the concentration of the at least one element contained in the sample.

This fluorescent X-ray analysis apparatus makes it possible to identify the sample type from the fluorescent X-ray spectrum obtained by preliminarily applying an X-ray to the sample, to determine appropriate measuring conditions (specifically, X-ray application parameters such as a measuring time, and a quantification method) the based on the result of the identification, and to control continuously and automatically the fluorescent X-ray analysis based on the determined measuring conditions. In other words, this fluorescent X-ray analysis apparatus automates the operations which has been conventionally carried out manually and enables the fluorescent X-ray analysis to be carried out more efficiently.

The fluorescent X-ray analysis method of the present invention includes a preliminary fluorescent X-ray analysis to identify whether the unknown sample is the nonmetal-based material or the metal-based material. This characteristic does not require an operator to obtain information as to the sample previously and to identify the sample type prior to the measurement, whereby the workload of the operator is reduced and the efficiency of the measurement is totally increased. Further, the fluorescent X-ray analysis method of the present invention makes it possible to select optimal conditions for the measurement and thereby the measuring time may not be longer than necessary, whereby the efficiency of the measurement is improved.

DETAILED DESCRIPTION OF THE PREFERRED EMBODIMENTS

According to the method of the present invention, an operator starts a measurement without previously setting measuring conditions, and carries out a short time irradiation of an X-ray at the initial stage of the measurement to detect and analyze an emitted fluorescent X-ray so that the rough composition of a sample is analyzed. The obtained rough composition is checked against, for example, a database hold in a fluorescent X-ray analysis apparatus, and the optimal measurement conditions are selected from the database depending on the composition. The measurement is continued under the selected conditions so as to display or output the concentrations of one or more particular elements contained in the sample and the accuracy thereof. The analysis for selecting the measuring conditions may be referred to as a preliminary measurement and the analysis under the selected measuring conditions may be referred to as a substantive measurement or a main measurement. The method of the present invention which involves the preliminary measurement and the substantive measurement is described together with an apparatus used for carrying out the method with reference to the drawings.

Figure 1:
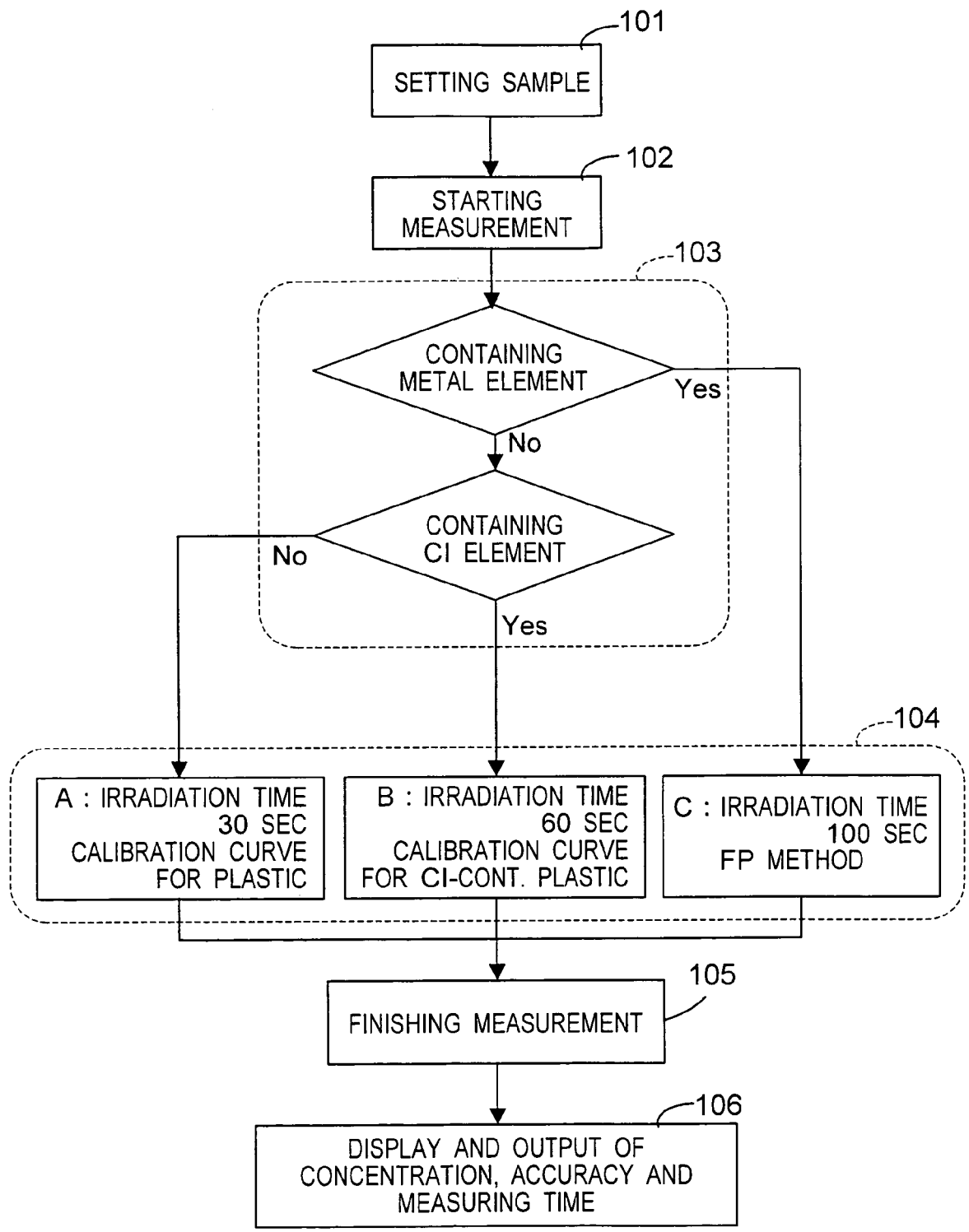
FIG. 1 shows a flowchart which describes one embodiment of the method of the present invention.
Figure 2:
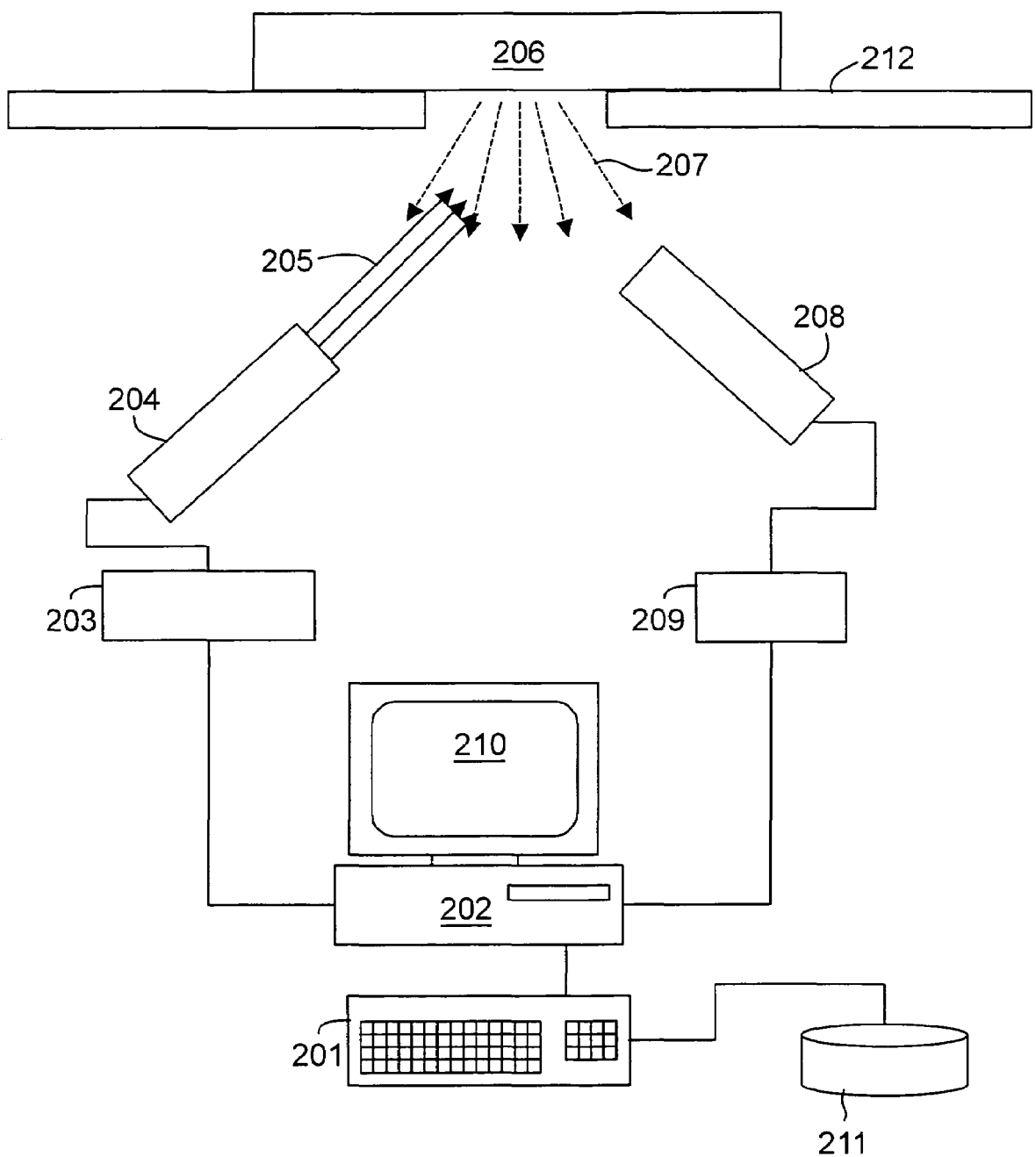
FIG. 2 is a schematic view of an apparatus for carrying out one embodiment of the method of the present invention.
Figure 3:
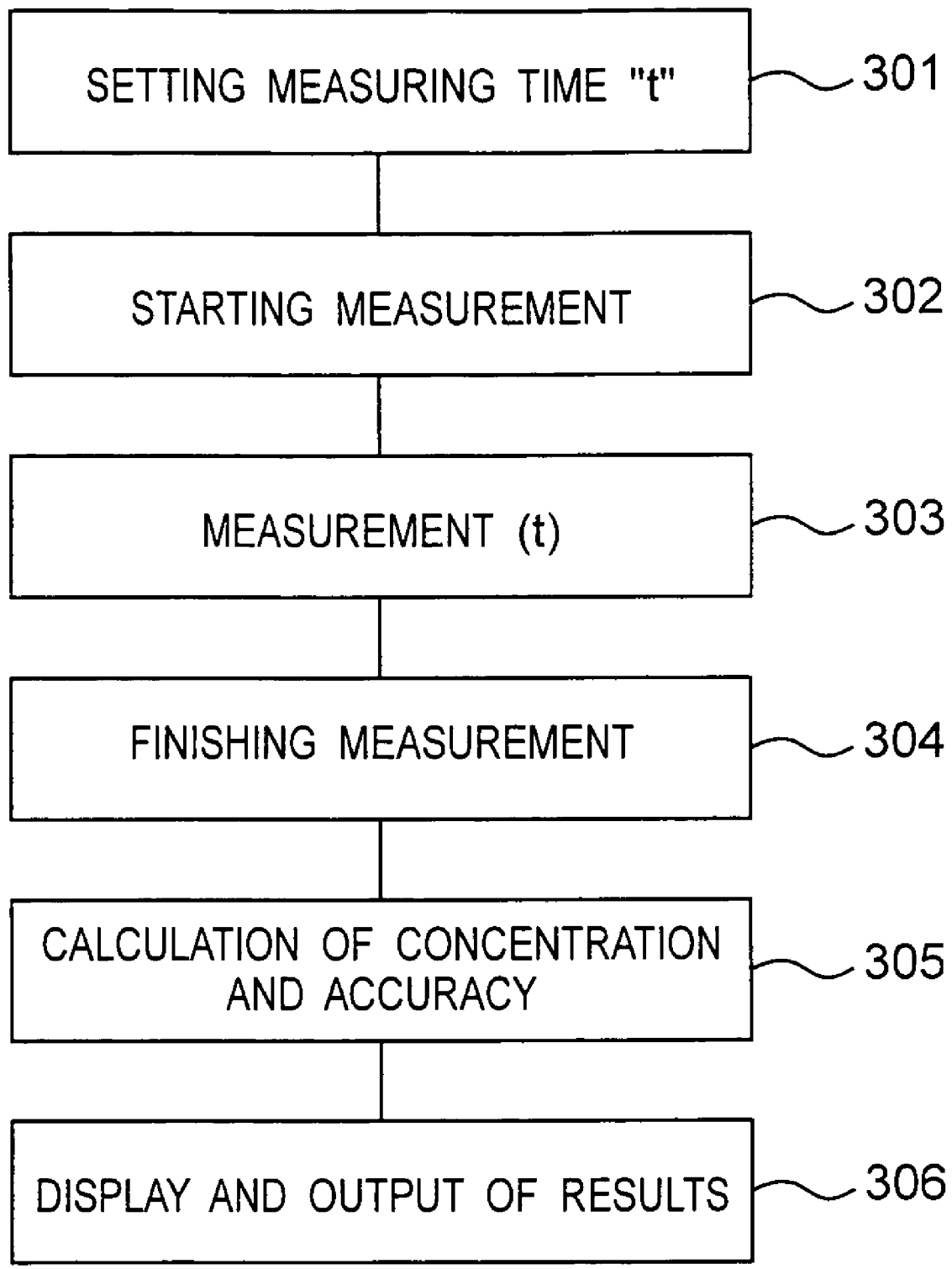
FIG. 3 is a flowchart which describes an example of a conventional method.

FIG. 1 is a flowchart explaining one embodiment of the method of the present invention. FIG. 2 is a schematic view of a fluorescent X-ray analysis apparatus which is used for carrying out the method of the present invention. In FIG. 2, a reference numeral 201 indicates an input part such as a keyboard. The input part 201 is used for inputting a sample name, conditions for evaluation, and an instruction for controlling a controller. A reference numeral 202 indicates an operation part where the operating process is carried out for signal processing of the evaluation conditions and quantification of a spectrum. A reference numeral 203 indicates the controller for controlling an applied voltage and an electric current in an X-ray tube. A reference numeral 204 indicates the X-ray tube which emits and radiates an X-ray. A reference numeral 205 indicates an emitted primary ray and a reference numeral 206 indicates a sample which is an object to be measured. A reference numeral 207 indicates a fluorescent X-ray and a reference numeral 208 indicates a detector which detects the fluorescent X-ray. A reference numeral 209 indicates an amplifier which amplifies the detected signals and a reference numeral 210 is a display unit for showing the results of the operation. A reference numeral 211 indicates an external memory device for storing information as to the sample and the results of the operation. A reference numeral 212 indicates a stage where the sample is positioned.

Next, a method for measuring the Cd concentration (X wt %: X % by weight) of an unknown sample using this apparatus is described. Firstly, the unknown sample is set in a sample chamber in the step 101 and the measurement is started (as in step 102). Specifically, the sample 206 is placed on the stage 212 as shown in FIG. 2, and the measurement is started with a key operation on the input part 201. A method for transmitting the signals for starting the measurement is not limited to the key input, and it may be carried out by another method. Various methods may be applicable. For example, some signals may be generated when the apparatus senses or detects that the sample is set on the stage. Alternatively, a lid may be provided above the stage and signals which are transmitted from a sensor which detects that the lid closes the apparatus may be used for the starting.

The instruction is sent from the operation part 202 to the controller 203 by the key input, and the controller 203 controls the voltage and the electric current in the X-ray tube 204 according to the instruction so that the primary ray 205 is applied to the sample 206. The fluorescent X-ray 207 is emitted from the sample 206 irradiated with the primary ray 205 and the energy and the intensity thereof are detected by the detector 208. The fluorescent X-ray signals detected by the detector 208 are amplified by the amplifier 209 and then sent to the operation part 202. The operation part 202 conducts the operation process to obtain a fluorescent X-ray spectrum and analyzes the rough composition of the sample to identify whether the sample 206 is nonmetal-based material or the metal-based material based on the spectrum (as in step 106 in FIG. 1).

In the step 103, identifying whether or not the sample 206 is a nonmetal-based material or metal-based material may be made by judging whether or not the sample contains iron (Fe), zinc (Zn), copper (Cu), or tin (Sn) as a metal element through the measurement of the intensity of the fluorescent X-ray emitted from at least one element selected from these metal elements. This is because that, in the case where a part which constitutes electronic or electric equipment is made of a metal-based material, at least one or more of these four elements is often contained as a main component. A metal element selected for the identification is not limited to these four elements, and another metal element may be selected in the step 103. In any case, when the middle element or the heavy element is contained as a main component in the sample, the fluorescent X-ray emitted from the middle or the heavy element has intensity which is significantly higher than those emitted from other elements.

When the sample is identified to be the nonmetal-based material, the step 103 further includes measuring an intensity of the fluorescent X-ray emitted from chlorine (Cl) and judging whether or not the sample contains Cl as a main component (that is, not as a impurity, but as an element constituting the main material). The reason for this is as follows: In the case where the main component of the sample 206 contains a compound having Cl (for example, vinyl chloride), the measuring conditions are preferably different from those for the other nonmetal-based material not containing Cl since the intensity of the fluorescent X-ray emitted from Cl is high. In the step 103, the intensity of the fluorescent X-ray emitted from bromine (Br) may be measured together with or in place of that of the fluorescent X-ray emitted from Cl. This is because the fluorescent X-ray emitted from Br, as well as Cl, has a high intensity. When the intensity of the fluorescent X-ray emitted from Br is high, the substantial measurement may be conducted employing the measurement conditions (for example, the measuring time and the calibration curve) for the bromine-based plastic resin. Detecting Cl may be conducted simultaneously with the identification whether or not the sample is the nonmetal-based material or the metal-based material (that is, the detection of Cl and the identification may be carried out in a single step).

The step 103 is intended to detect the main component of the unknown sample. In the step 103, the element such as Fe, Zn, Cu, Sn, Cl or Br whose existence is sensed by applying the X-ray for a relatively short time is measured, and therefore X-ray irradiation conditions are not required to be restricted in detail. The step 103 may be carried out under a voltage selected from a general voltage range (about 5 KV to about 50 KV) and a electric current value which is automatically adjusted based on an amount of a fluorescent X-ray which enters in the detector (about several microampere to 1 mA). The measuring time (the X-ray irradiation time) is set so that it is sufficient to judge whether or not the main component is metal. Specifically, the sample 206 is irradiated with the X-ray 205 for about 1 second to about 10 seconds.

Based on the result of the analysis in the step 103, the measurement conditions for the sample 206 are determined. The conditions to be determined are, for example, the measuring time and the quantification method. In the illustrated embodiment, any one of the following three types is selected as the measuring conditions.

A. Conditions for plastic resin base (in the case where the four metal elements are not detected)
X-ray irradiation time: 30 seconds;
Quantification method: plastic base calibration curve.

B. Conditions for chloride-containing plastic (in the case where the four metal elements are not detected and only chlorine is detected)
X-ray irradiation time: 60 seconds;
Quantification method: Chloride-containing plastic base calibration curve.

C. Conditions for metal (in the case where at least one of the four metal elements is detected as a main component)
X-ray irradiation time: 100 seconds;
Quantification method: FP method.

Herein, a parameter of the measuring conditions is the actual X-ray irradiation time, but the parameter is not limited thereto. Other parameters which determine the measurement conditions include the voltage and electric current in the X-ray tube, the type of a filter, an effective measuring time (a live time) and a dead time. It is possible to conduct the analysis more precisely and faster by using these parameter together with or in place of the X-ray irradiation time.

The determination of the measurement conditions may be carried out by checking the result obtained in the step 103 against the data stored in the external memory device 212, using the operation part 202. In the external memory device 212, the data as to the result of the preliminary measurement and the optimal measurement conditions for various materials are stored. As the larger number of data is stored in the device 212, more optimal measurement conditions can be selected. These data may be stored in the operation part 202.

Next, an instruction to start the substantive measurement is transmitted from the operation part 202 to the controller 203 based on the selected measurement conditions (as in step 104 in FIG. 1). The controller 203 controls the irradiation conditions of the X-ray tube 204 as desired so that the primary ray 205 is applied to the sample 206 for only a desired time. The fluorescent X-ray 207 emitted from the sample 206 is detected by the detector 208, amplified by the amplifier 209 and subjected to the operation process which is conducted by the operation part 202. After the predetermined measurement has been finished, the Cd concentration (X wt %) in the sample and the accuracy (error) thereof are calculated by the operation part 202 (as in step 105 in FIG. 1).

The techniques for finishing or stopping the measurement may be a technique of stopping the irradiation of the primary ray 205 from the X-ray tube 204 by controlling the controller 203, a technique of stopping the detection conducted by the detector 208, and a technique of providing a shutter in a light path of the primary ray 205 or the fluorescent X-ray 207, but not limited thereto. Further, the operation process may be continued for fixing display and output of the operation result. Alternatively, these operations may be conducted in parallel.

The operation results of the step 105 (specifically, the Cd concentration, the accuracy (error) and the actual measuring time) are displayed on the display device 210 and output by a printer or another outputting device (as in step 106 in FIG. 1).

As describe above, this embodiment does not require that the type of sample is judged relying on five senses of the operator. The rough identification of the sample, the selection of the optimal measurement conditions and the measurement of the content of a trace element(s) can be carried out continuously and automatically. Therefore, the method of the present invention makes it possible to reduce the measuring time and improve the operationality.

In this embodiment, the preliminary identification is carried out by detecting one or more of the four elements, that is, Fe, Cu, Zn, and Sn, and detecting Cl as a nonmetal element for identifying the sample. An appropriate element should be selected and detected in the preliminary identification depending on a type of unknown sample, required analysis accuracy, and an analysis speed, and it is not limited to these four elements. Further, not only the measuring time, but also the voltage and the electric current of the x-ray tube may be preferably changed so as to conduct the substantive measurement under more appropriate measurement conditions. The measurement time may be determined by a method wherein the ending time of the measurement is determined depending on the rates of the concentration and accuracy.

The result may be displayed on the display unit 210 and stored in the external storage device 211 simultaneously, resulting in a more solid database. It is preferable that other information such as the size, the shape, and the material of the sample is stored in the external memory device 211, in addition to the Cd concentration, the measurement accuracy and the measuring time.

After finishing the measurement, the sample 206 needs to be brought out. If the primary ray 205 is still emitted upon bringing out the sample, the safety of the operator may not be secured. Therefore, the primary ray 205 is preferably stopped promptly after the measurement has been finished. Specifically, a stop signal is preferably transmitted to the controller 203 through the operation part 202 after the measurement has been finished in the step 106 and it is confirmed that the result is shown in the display unit 210. In this case, the controller 203 serves to stop the action of the X-ray tube 204.

The method for securing the safety of the operator may be a technique of controlling the controller 203 to stop the irradiation of the primary ray 205 emitted from the X-ray tube 204, a technique of stopping the detection conducted by the detector 208, or a technique of providing a shutter in a light path of the primary ray 205, but not limited thereto.

In this embodiment, the method for measuring the Cd element concentration by using any of the three types of the measuring conditions. The concentration of another element (s) in addition to Cd may be measured at the same time. In that case, the measuring conditions to be stored in the external memory device may be further segmented and the measuring conditions may be selected from more various measuring conditions. Further, the measurement of the concentration(s) of the trace element(s) and a simple quantification may be carried out in parallel, and the results thereof may be stored as the data, whereby the measuring conditions are further segmented and more particular measuring conditions may be selected when the analysis is conducted for another sample later.

The types of the measurement conditions may be classified into, for example, conditions for a plastic containing no chlorine, a chlorine-containing plastic, a bromine-containing plastic, iron, copper, a solder material, Si-glass, F-glass, P-glass, and rubber, and the parameters for each type may be previously set. The sample is judged to belong to what type of these materials by the preliminary measurement, and subjected to the substantial measurement according to the measuring conditions assigned to the judged material type. The types mentioned herein are exemplary and does not limit the scope of the present invention.

When the information is available previously, the measurement conditions may be input based on the information, and these conditions and the measurement conditions determined based on the results of the preliminary measurement may be employed together, whereby a higher accuracy and a higher speed can be achieved in the measurement. It should be noted that this information is not necessarily required and this (that is, an unknown sample can be analyzed without the information) is a characteristic of the present invention.

The fluorescent X-ray analysis method of the present invention does not require distinguishing the samples by a human's eye nor obtaining the information as to the sample previously from a supplier, and makes it possible to judge the sample type by a preliminary fluorescent X-ray analysis and to carry out a quantitative analysis of the trace sample(s) employing the measurement conditions adapted to the sample type. Therefore, the method of the present invention is preferably used to measure the trace element(s) contained in various parts constituting the electronic or electric equipment quickly and accurately in order to judge whether or not the concentration of particular element(s) satisfies the standards stipulated in a law or the like.

What is claimed is:

1. A fluorescent X-ray analysis method comprising the steps of:
   (1) applying an X-ray to a sample;
   (2) classifying the sample a nonmetal-based material or a metal-based material;
   (3) accessing a predetermined list of measuring conditions for the X-ray analysis;
   (4) selecting a measuring condition from the predetermined list based on the classification of the sample;
   (5) controlling the application of the X-ray to the sample according to the selected measuring condition; and
   (6) measuring a concentration of at least one element contained in the sample with application of the X-ray according to the selected measuring condition.

2. The fluorescent X-ray analysis method according to claim 1, further comprising the step of detecting whether or not the sample contains any one of Cl and Br.

3. The fluorescent X-ray analysis method according to claim 2, wherein the step of detecting is performed concurrently with Step (1).

4. The fluorescent X-ray analysis method according to claim 1, wherein the sample is classified as the metal-based material when the at least one element selected from a group consisting of Fe, Zn, Cu and Sn is detected.

5. The fluorescent X-ray analysis method according to claim 1, wherein the sample is classified as a nonmetal-based material when a main component of the sample emits substantially no fluorescent X-ray further to Step (1).

6. The fluorescent X-ray analysis method according to claim 5, wherein the sample is classified as the metal-based material when the sample emits an fluorescent X-ray of an amount greater than an amount for the sample of claim 5.

7. The fluorescent X-ray analysis method according to claim 1, wherein the sample is classified as a metal-based material if it contains an element having an atomic number that is at least sixteen (16).

8. A fluorescent X-ray analysis apparatus comprising: a sample stage for holding a sample;
   an X-ray tube positioned relative to the sample stage for applying an X-ray;
   and a detector positioned relative to the sample stage for detecting an emitted X-ray;

and an operation instrument for controlling the X-ray tube and receiving communication from the detector corresponding to the detected emitted fluorescent X-ray, the operation instrument configured to perform the following steps:
(1) classifying the sample as a nonmetal-based material or a metal-based material based on the communication received from the detector;
(2) selecting a measuring process condition from a predetermined list of measuring process conditions based on the classification of the sample; and
(3) controlling the X-ray tube so that concentration of at least one element contained in the sample is measured according to the selected measuring condition; and
(4) determining the concentration of the at least one element contained in the sample.

9. The fluorescent X-ray analysis apparatus according to claim 8, which further comprise a memory for storing the predetermined list.

* * * * *